(12) United States Patent
Van Bladel et al.

(10) Patent No.: US 11,744,615 B2
(45) Date of Patent: Sep. 5, 2023

(54) PERICARDIAL INFLATION CATHETER AND SYSTEMS AND METHODS EMPLOYING SAME

(71) Applicant: BioVentrix, Inc., San Ramon, CA (US)

(72) Inventors: Kevin Van Bladel, San Ramon, CA (US); Lon S. Annest, New York, NY (US); Michael S. Dana, Fremont, CA (US)

(73) Assignee: BioVentrix, Inc., San Ramon, CA (US)

( * ) Notice: Subject to any disclaimer, the term of this patent is extended or adjusted under 35 U.S.C. 154(b) by 392 days.

(21) Appl. No.: 17/031,435

(22) Filed: Sep. 24, 2020

(65) Prior Publication Data
US 2022/0087715 A1    Mar. 24, 2022

(51) Int. Cl.
*A61B 17/34*      (2006.01)
*A61B 17/00*      (2006.01)

(52) U.S. Cl.
CPC .... *A61B 17/3474* (2013.01); *A61B 17/00234* (2013.01); *A61B 17/3423* (2013.01); *A61B 2017/003* (2013.01); *A61B 2017/00247* (2013.01); *A61B 2017/3425* (2013.01); *A61B 2217/007* (2013.01)

(58) Field of Classification Search
CPC ..... A61B 17/00; A61B 17/34; A61B 17/3417; A61B 17/3496; A61B 17/3474; A61B 17/3423; A61B 17/00234; A61B 2017/00247; A61B 2017/003; A61B 2017/3425; A61B 2019/481
See application file for complete search history.

(56) References Cited

U.S. PATENT DOCUMENTS

| | | | |
|---|---|---|---|
| 5,295,958 A | * | 3/1994 | Shturman ........... A61M 60/896 606/159 |
| 7,441,342 B2 | | 11/2008 | Annest et al. |
| 8,425,402 B2 | | 4/2013 | Annest et al. |
| 9,039,594 B2 | | 5/2015 | Annest et al. |
| 9,937,043 B2 | | 4/2018 | Van Bladel et al. |
| 10,219,904 B2 | | 2/2019 | Butler et al. |
| 10,335,279 B2 | | 2/2019 | Chin et al. |
| 10,314,498 B2 | | 6/2019 | Van Bladel et al. |
| 10,398,557 B2 | | 9/2019 | Chin et al. |
| 10,478,305 B2 | | 11/2019 | Annest et al. |
| 10,575,953 B2 | | 3/2020 | Van Bladel et al. |
| 10,588,613 B2 | | 3/2020 | Moshe et al. |
| 10,617,524 B2 | | 4/2020 | Van Bladel et al. |
| 10,617,525 B2 | | 4/2020 | Annest et al. |
| 10,624,744 B2 | | 4/2020 | Annest et al. |
| 10,624,745 B2 | | 4/2020 | Chin et al. |

(Continued)

*Primary Examiner* — Vi X Nguyen
(74) *Attorney, Agent, or Firm* — Nixon & Vanderhye P.C.

(57) ABSTRACT

A method for performing a therapeutic intervention in a pericardial space of a heart includes delivering a catheter into a right atrium of the heart and steering the catheter so that a distal end of the catheter is positioned adjacent an access site in the right atrium. The distal end of the catheter is anchored in a heart wall of the right atrium adjacent the access site and the heart wall is inverted to separate an exterior surface of the inverted heart wall from contact with parietal pericardial tissue. The inverted heart wall is penetrated to provide access to the pericardial space around the heart. A device is delivered through the penetrating in the inverted heart wall to perform the therapeutic intervention in the pericardial space.

22 Claims, 13 Drawing Sheets

(56) References Cited

U.S. PATENT DOCUMENTS

| | | |
|---|---|---|
| 10,631,982 B2 * | 4/2020 | Hammer .............. A61F 2/2409 |
| 10,660,753 B2 | 5/2020 | Pham et al. |
| 11,051,941 B2 | 7/2021 | Annest et al. |
| 11,051,942 B2 | 7/2021 | Van Bladel et al. |
| 11,185,414 B2 | 11/2021 | Van Bladel et al. |
| 2017/0216032 A1 | 8/2017 | Van Bladel et al. |
| 2018/0193600 A1 | 7/2018 | Kassab et al. |

* cited by examiner

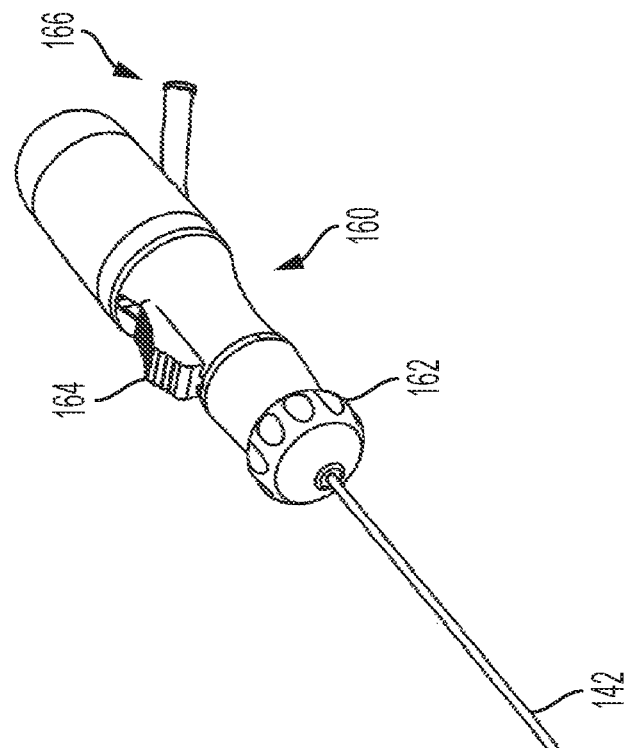
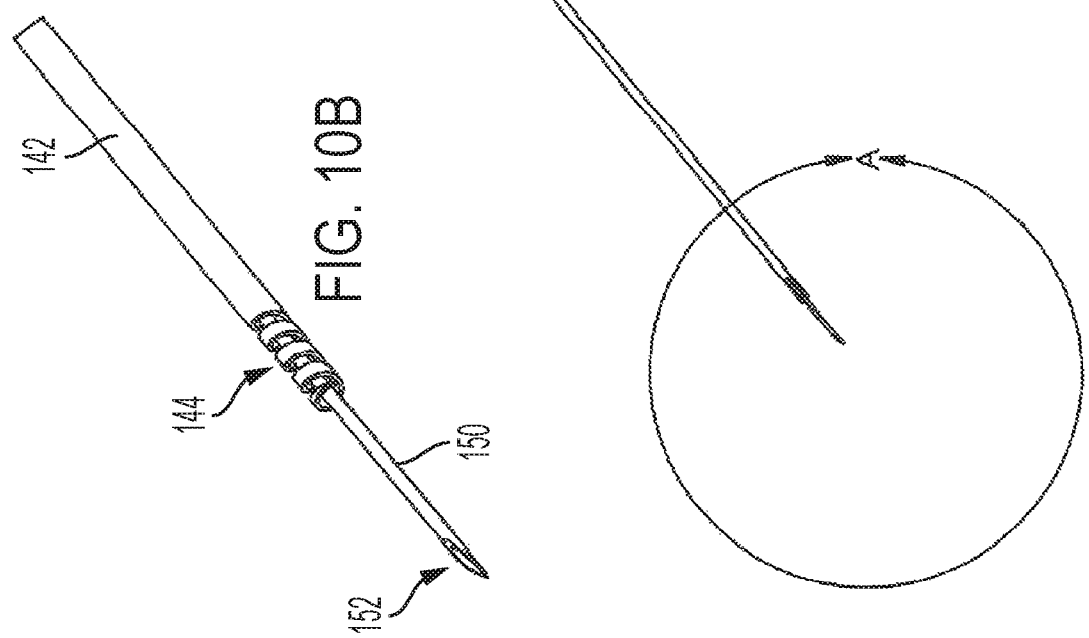
FIG. 10A
FIG. 10B

PERICARDIAL INFLATION CATHETER AND SYSTEMS AND METHODS EMPLOYING SAME

BACKGROUND

Heart implants are currently used to resize or alter the geometry of a ventricle in a failing heart, such as by reducing its radius of curvature through the process of excluding a portion of the circumference of the chamber, and thereby reduce wall stress on the heart and improve the heart's pumping performance. Congestive heart failure may, for example, be treated using one or more implants which are selectively positioned relative to a first wall of the heart (typically an interventricular septum), and another wall of the heart so as to exclude scar tissue and limit a cross sectional area, or distance across a ventricle. Functional deterioration of the heart tissues may be inhibited by decreasing a size of the heart chamber and/or approximating tissues so that stress on the tissues is limited.

Congestive heart failure (sometimes referred to as "CHF" or "heart failure") is a condition in which the heart does not pump enough blood to the body's other organs. Congestive heart failure may in some cases result from narrowing of the arteries that supply blood to the heart muscle, high blood pressure, heart valve dysfunction due to degenerative processes or other causes, cardiomyopathy (a primary disease of the heart muscle itself), congenital heart defects, infections of the heart tissues, and the like. However, in many cases congestive heart failure may be triggered by a heart attack or myocardial infarction. Heart attacks can cause scar tissue that interferes with the heart muscle's healthy function, and that scar tissue can progressively replace more and more of the contractile heart tissue. More specifically, the presence of the scar may lead to a compensatory neuro-hormonal response by the remaining, non-infarcted myocardium leading to progressive dysfunction and worsening failure. The scar tissue thins over time and causes the heart chamber to expand in volume.

People with heart failure may have difficulty exerting themselves, often becoming short of breath, tired, and the like. As blood flow out of the heart decreases, pressure within the heart increases. Not only does overall body fluid volume increase, but higher intracardiac pressure inhibits blood return to the heart through the vascular system. The increased overall volume and higher intracardiac pressures result in congestion in the tissues. Edema or swelling may occur in the legs and ankles, as well as other parts of the body. Fluid may also collect in the lungs, interfering with breathing (especially when lying down). Congestive heart failure may also be associated with a decrease in the ability of the kidneys to remove sodium and water, and the fluid buildup may be sufficient to cause substantial weight gain. With progression of the disease, this destructive sequence of events can cause the progressive deterioration and eventual failure of the remaining functional heart muscle.

Treatments for congestive heart failure may involve rest, dietary changes, and modified daily activities. Various drugs may also be used to alleviate detrimental effects of congestive heart failure, such as by dilating expanding blood vessels, improving and/or increasing pumping of the remaining healthy heart tissue, increasing the elimination of waste fluids, and the like.

Surgical interventions have also been applied for treatment of congestive heart failure. If the heart failure is related to an abnormal heart valve, the valve may be surgically replaced or repaired. Techniques also exist for exclusion of the scar and volume reduction of the ventricle. These techniques may involve (for example) surgical left ventricular reconstruction, ventricular restoration, the Dor procedure, and the like. If the heart becomes sufficiently damaged, even more drastic surgery may be considered. For example, a heart transplant may be the most viable option for some patients. These surgical therapies can be at least partially effective, but typically involve substantial patient risk. While people with mild or moderate congestive heart failure may benefit from these known techniques to alleviate the symptoms and/or slow the progression of the disease, less traumatic, and therefore, less risky therapies which significantly improve the heart function and extend life of congestive heart failure patients has remained a goal.

It has been proposed that an insert or implant be used to reduce ventricular volume of patients with congestive heart failure. With congestive heart failure, the left ventricle often dilates or increases in size. This can result in a significant increase in wall tension and stress. With disease progression, the volume within the left ventricle gradually increases and blood flow gradually decreases, with scar tissue often taking up a greater and greater portion of the ventricle wall. By implanting a device which brings opposed walls of the ventricle into contact with one another, a portion of the ventricle may be excluded or closed off. By reducing the overall size of the ventricle, particularly by reducing the portion of the functioning ventricle chamber defined by scar tissue, the heart function may be significantly increased and the effects of disease progression at least temporarily reversed, halted, and/or slowed.

BRIEF DESCRIPTION

The embodiments described herein are particularly useful for anchoring a catheter within the right atrium at an access site to provide access to a pericardial space of the heart for performance of a therapeutic intervention or procedure. For example, the embodiments may be particularly useful for anchoring a catheter within the right atrial appendage and for insufflating a pericardial space around the heart. For example, a catheter may be placed into the right atrium of the heart, typically from either the femoral or jugular vein. The catheter may be steered within the right atrium to the access site, such as into the right atrial appendage, and anchored within a heart wall of the right atrium at the access site. The catheter may be anchored within the heart wall using an anchoring member, such as a screw tip that is positioned within a funnel tip catheter. Concentric to both of these devices may be a perforating device, such as a needle, that can be advanced from outside the body using a slidable handle.

After the device is positioned within the right atrium at the access site, the anchoring member may engage the heart wall. The heart wall may then be inverted within the funnel tip of the catheter, which may allow the perforating device to be advanced safely outside the heart wall. A therapeutic intervention may then be performed in the pericardial space of a heart. For example, the needle or anchoring member can insufflate the pericardium around the heart to give a physician space between the heart wall and the pericardium to perform one or more therapeutic procedures. The process of insufflating the pericardial space may be particularly important in providing sufficient space to place anchors percutaneously from inside the heart. The therapeutic procedure may alternatively involve monitoring a pressure outside of the heart, positioning a heart implant or instrument exterior to the heart, irrigating an exterior of the heart, applying suction to control bleeding, draining pericardial fluid, performing an epicardial biopsy, mapping a portion of the heart, pacing the heart, or any other procedure.

According to a first aspect, a method for performing a therapeutic intervention in a pericardial space of a heart includes delivering a catheter into a right atrium of the heart and steering the catheter within the right atrium so that a distal end of the catheter is positioned adjacent an access site in the right atrium. The method also includes anchoring the distal end of the catheter in a heart wall of the right atrium adjacent the access site and inverting the heart wall at the access site to separate an exterior surface of the inverted heart wall from contact with parietal pericardial tissue. The method further includes penetrating the inverted heart wall at the access site to provide access to the pericardial space of the heart and delivering a device through the penetration in the inverted heart wall to perform the therapeutic intervention in the pericardial space of the heart between the visceral and parietal pericardium.

Anchoring the distal end of the catheter in the heart wall may include engaging the heart wall with an anchoring member that is disposed within a lumen of the catheter. The anchoring member may be a rotatable screw, a barb that is able to grasp the heart wall, a hook, a snare, a suction device, or any other tissue engaging member. The anchoring member may be retracted to invert the heart wall of the right atrium at the access site. In such embodiments, the anchoring member may be retracted to pull the heart wall into a conically shaped end of the catheter.

The device that is delivered through the penetration in the inverted heart wall may be a catheter, a perforating device, a hollow needle, a heart anchor, a lead, or any other tissue penetrating device. In a specific embodiment, the inverted heart wall is penetrated with a perforating device, such as a needle, a laser, an RF energy device, and the like. For example, penetrating the inverted heart wall may include extending a needle through the inverted heart wall. In such embodiments, the needle may be positioned concentrically relative to the anchoring member. The method may additionally include delivering gas or fluid into the pericardial space through a lumen of the needle to insufflate the pericardial space. Alternatively, gas or fluid may be delivered into the pericardial space through a lumen of the anchoring member to insufflate the pericardial space.

In a specific embodiment, the access site may be a right atrial appendage of the heart, or any other appropriate site in the right atrium. The delivery catheter may include multiple tips and one of the tips may be positioned in the right atrial appendage or any other selected access site. The therapeutic intervention that is performed in the pericardial space may include insufflating the pericardial space, monitoring a pressure outside of the heart, positioning a heart implant or instrument exterior to the heart, irrigating an exterior of the heart, suctioning bleeding, draining pericardial fluid, performing an epicardial biopsy, mapping a portion of the heart, pacing the heart, or any other therapeutic procedure. In a specific embodiment, the therapeutic intervention includes delivering gas or fluid into the pericardial space to insufflate the pericardial space such as to interrupt parietal and visceral pericardial-surface contact.

According to another aspect, a system for accessing a pericardial space of a heart includes a delivery catheter that includes an elongate body, an anchoring member, a perforating device, a handle mechanism, and an access port. The elongate body has a proximal end, a distal end, and a lumen that extends between the proximal end and the distal end. The anchoring member is positioned within the lumen of the elongate body and is extendible therefrom. The perforating device is also positioned within the lumen of the elongate body and is extendible therefrom. The handle mechanism is positioned on the proximal end of the elongate body and the access port is coupled with the distal end of the elongate body so that a device, gas, or fluid are deliverable through the access port and to the distal end of the elongate body. The delivery catheter is configured so that the elongate body is deliverable through a vasculature of a body and into a right atrium of the heart so that the distal end of the elongate body is positionable adjacent an access site of the right atrium. The anchoring member is extendible from the lumen of the elongate body and into a heart wall at the access site to secure the distal end of the elongate body to the heart wall. The perforating device is extendible from the lumen of the elongate body and through the inverted heart wall to provide access to the pericardial space of the heart so as to enable the device, or gas or fluid, to be delivered into the pericardial space.

The system may also include a gas or fluid source that is coupleable with the access port of the delivery catheter to provide gas or fluid to the delivery catheter. In such embodiments, gas or fluid is deliverable from the gas or fluid source, through the access port, and into the pericardial space via a perforation in the heart wall at the access site. The gas or fluid that is delivered into the pericardial space may insufflate the pericardial space.

In a specific embodiment, the anchoring member is a screw member or screw tip and the perforating device is a needle that is positioned concentrically within the screw member. In such embodiments, the handle mechanism may include a first member and a second member. The first member may be operably coupled with the screw member so that a user actuation of the first member causes the screw member to extend from the lumen of the elongate body and into a heart wall at the access site. The second member may be operably coupled with the needle so that a user actuation of the second member causes the needle to penetrate the heart wall at the access site.

In some embodiments, the system also includes a needle that is configured to penetrate an exterior wall and a septal wall of the heart and a heart anchor delivery catheter that is configured to deliver a heart anchor into the heart and adjacent to the septal wall or the exterior wall. The system may additionally include a heart implant that includes a first anchor that is configured for positioning on the septal wall of the heart, a second anchor that is configured for positioning on the exterior wall of the heart, and an elongate tension member. The elongate tension member may have a first end that is coupled with the first anchor and a second end that is coupled with the second anchor. The elongate tension member may be configured to extend from the first anchor, through the septal wall, through a left ventricle of the heart, and through the exterior wall such that applying tension between the first and second anchors with the tension member urges the septal wall and the exterior wall into engagement. When the second anchor is positioned on the exterior wall, the second anchor may be disposed within the pericardium.

According to another aspect, a catheter for accessing a pericardial space of a heart includes an elongate body, an anchoring member, a tissue penetrating member, and a handle mechanism. The elongate body has a proximal end, a distal end, and a lumen that extends between the proximal end and the distal end. The elongate body is configured for insertion within a vasculature of a patient so that the distal end of the elongate body is positionable in a right atrium of the heart. The anchoring member is positioned within the lumen of the elongate body and is extendible distally of the elongate body. The anchoring member is configured to anchor within a heart wall of the right atrium at the access site to secure the distal end of the elongate body to the heart wall. The tissue penetrating member is positioned within the lumen of the elongate body. The tissue penetrating member is configured to penetrate the heart wall at the access site to provide access to the pericardial space of the heart. The handle mechanism is positioned on the proximal end of the elongate body and may include a first member and a second member. The first member may be operably coupled with the anchoring member so that a user actuation of the first member causes the anchoring member to extend distally of the elongate body. The second member may be operably coupled with the tissue penetrating member so that a user actuation of the second member causes the tissue penetrating member to penetrate the heart wall at the access site.

In some embodiments, the anchoring member may be a rotatable screw, a barb, a hook, a snare, or a suction device. In a specific embodiment, the anchoring member may be a screw member or screw tip that is configured to screw into the heart wall. The screw member/tip may be retractable within the lumen of the elongate body. In such embodiments, the distal end of the elongate body may be expandable into a funnel or conical shape so that retraction of the screw member/tip causes the heart wall to retract into the funnel or conically shaped distal end of the elongate body. The tissue penetrating device may be a needle that is positioned concentrically within the screw member.

In some embodiments, the catheter may also include a gas or fluid access port that is fluidly coupled with the distal end of the elongate body. The gas or fluid access port may be configured to receive an insufflation gas or fluid that is deliverable to the pericardial space to insufflate the pericardial space. The needle may be hollow and may be fluidly coupled with the gas or fluid access port so that the insufflation gas or fluid is deliverable through the needle and into the pericardial space.

BRIEF DESCRIPTION OF THE DRAWINGS

The present invention is described in conjunction with the appended figures:

FIGS. 10A-B illustrate an embodiment of the anchoring member and tissue penetrating member.

Figure 1:
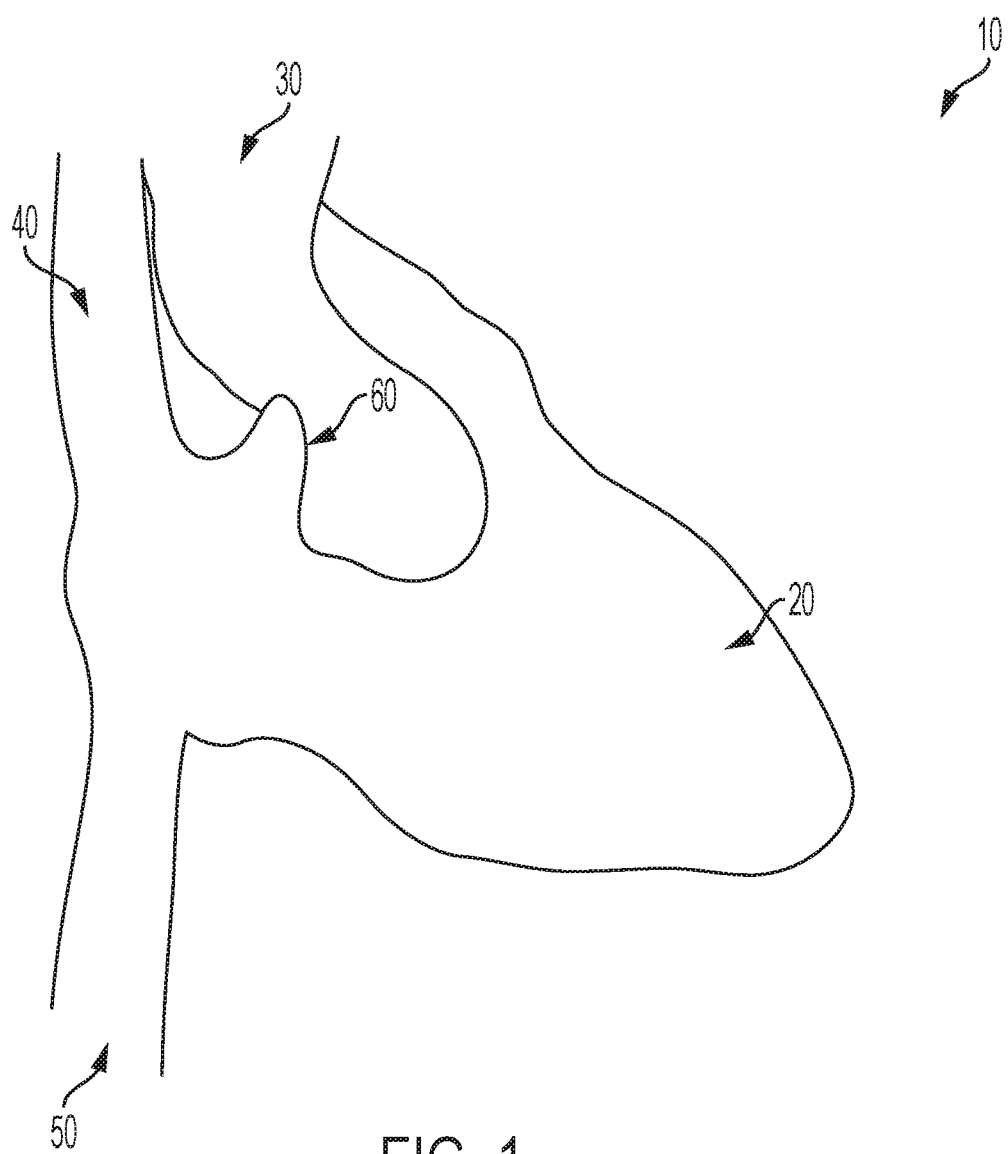
FIG. 1 illustrates an access to the right atrium of the heart from the femoral and jugular veins.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

The embodiments described herein are directed toward devices and methods for accessing a pericardial space of the heart in order to perform one or more therapeutic interventions or procedures on or involving the heart. Exemplary therapeutic intervention that may be performed in the pericardial space include insufflating the pericardial space, monitoring a pressure outside of the heart, positioning a heart implant or instrument exterior to the heart, irrigating an exterior of the heart, suctioning bleeding, draining pericardial fluid, performing an epicardial biopsy, mapping a portion of the heart, pacing the heart, and the like. In a specific embodiment, the therapeutic intervention includes delivering gas or fluid into the pericardial space to insufflate the pericardial space such as to interrupt parietal and visceral pericardial-surface contact. For ease in describing the embodiments herein, the description will mainly focus on procedures in which the pericardial space is insufflated. It should be recognized, however, that various other procedures, including those specifically mentioned herein, may be performed in place of, or in addition to, insufflating the pericardial space.

To perform the therapeutic intervention, a device may be inserted into the pericardial space through a perforation or penetration in a heart wall at an access site. To position or insert the device into the pericardial space, a catheter may be positioned within the right atrium of the heart at or adjacent to an access site. An anchoring member may engage the heart wall at the access site and the heart wall may be inverted at the access site. The anchoring member may be retracted to invert the heart wall of the right atrium at the access site. In some embodiments, the heart wall may be inverted within a funnel tip of the catheter, which may allow a perforating device to be advanced through the heart wall and safely into the pericardial space. The therapeutic device may then be inserted through a perforation or penetration in the heart wall that is formed via the perforating device and the therapeutic intervention may be performed in the pericardial space of a heart.

The anchoring member may be a rotatable screw, a barb that is able to grasp the heart wall, a hook, a snare, a suction device, or any other tissue engaging member. For ease in describing the embodiments herein, the anchoring member will be generally referred to as a screw member, although it should be recognized that the illustrated screw member may represent any anchoring member including those specifically described herein. Similarly, it should be realized that the various anchoring members described or contemplated herein may be substituted for the screw member that is described hereinafter. The perforating member may be a needle, a laser, an RF energy device, and the like. For ease in describing the embodiments herein, the perforating device will be generally referred to as a needle, although it should be recognized that the illustrated needle may represent any perforating device including those specifically described herein. Similarly, it should be realized that the various perforating devices described or contemplated herein may be substituted for the needle that is described hereinafter.

In a specific embodiment, the area around the heart may be insufflated to create separation between the heart and pericardium to enable delivery of heart anchors to an external heart wall of the heart. To insufflate the area around the heart, an insufflating device may be positioned at the access site in the right atrium or another chamber of the heart. In a specific embodiment, the insufflating device may be positioned in a right atrial appendage of the heart. The insufflation device may gain access to the access site (e.g., the right atrial appendage) via pericardial access through the jugular or femoral veins.

When the insufflation device is positioned in the right atrial appendage, a needle may be inserted across tissue in the right atrial appendage so that a distal end of the needle is positioned within a space between the heart and pericardium. A fluid or gas may then be delivered from the needle or insufflation device to insufflate the space between the heart wall and pericardium.

Figures 12A, 12B:
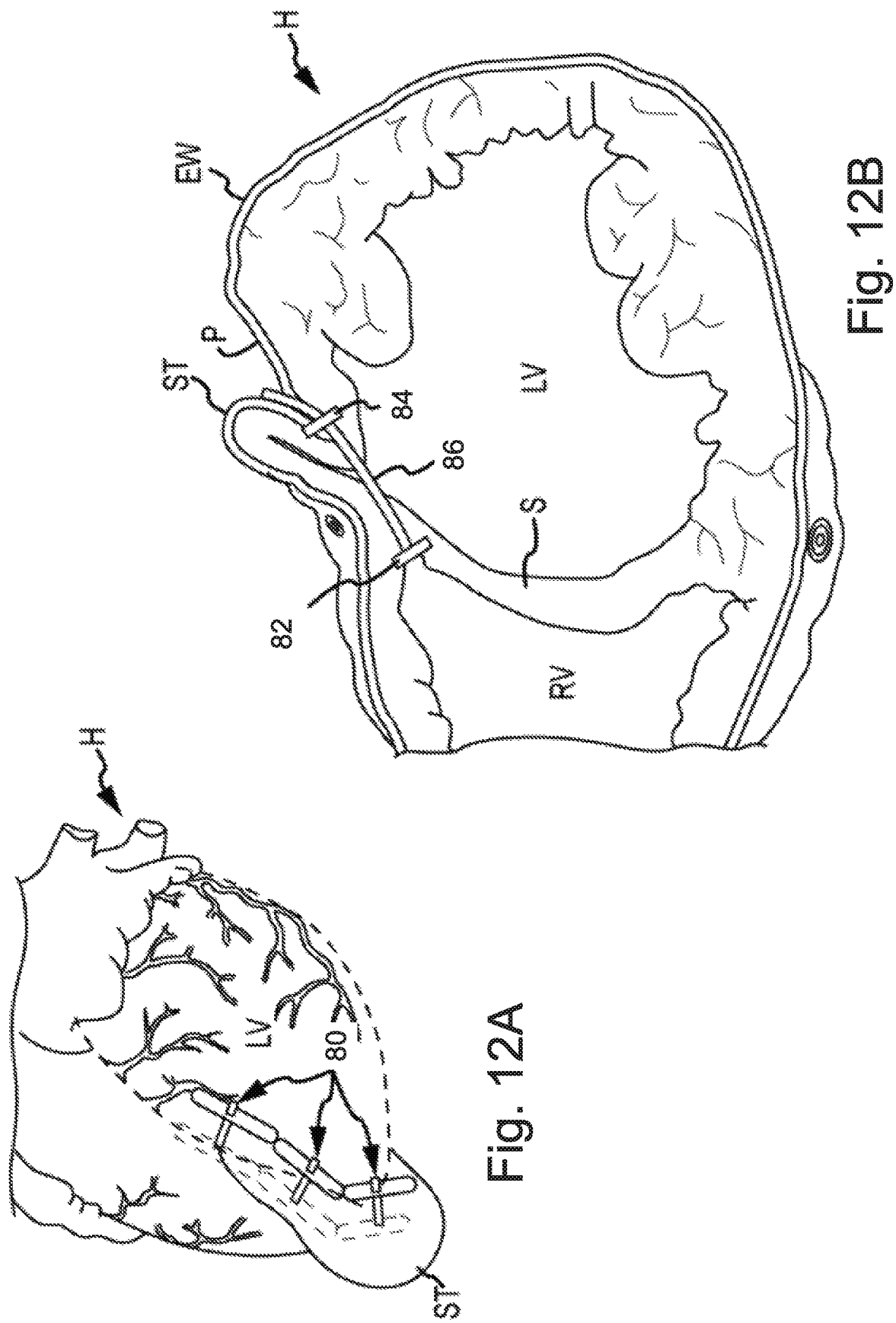
FIG. 12A illustrates a reconstructed left ventricle using a series of implanted anchors so as to mitigate the deleterious effects of congestive heart failure.
FIG. 12B illustrates a cross-sectional view of the heart of FIG. 12A, showing a reduction in the size of the left ventricle effected by one of the implants.
Figure 12C:
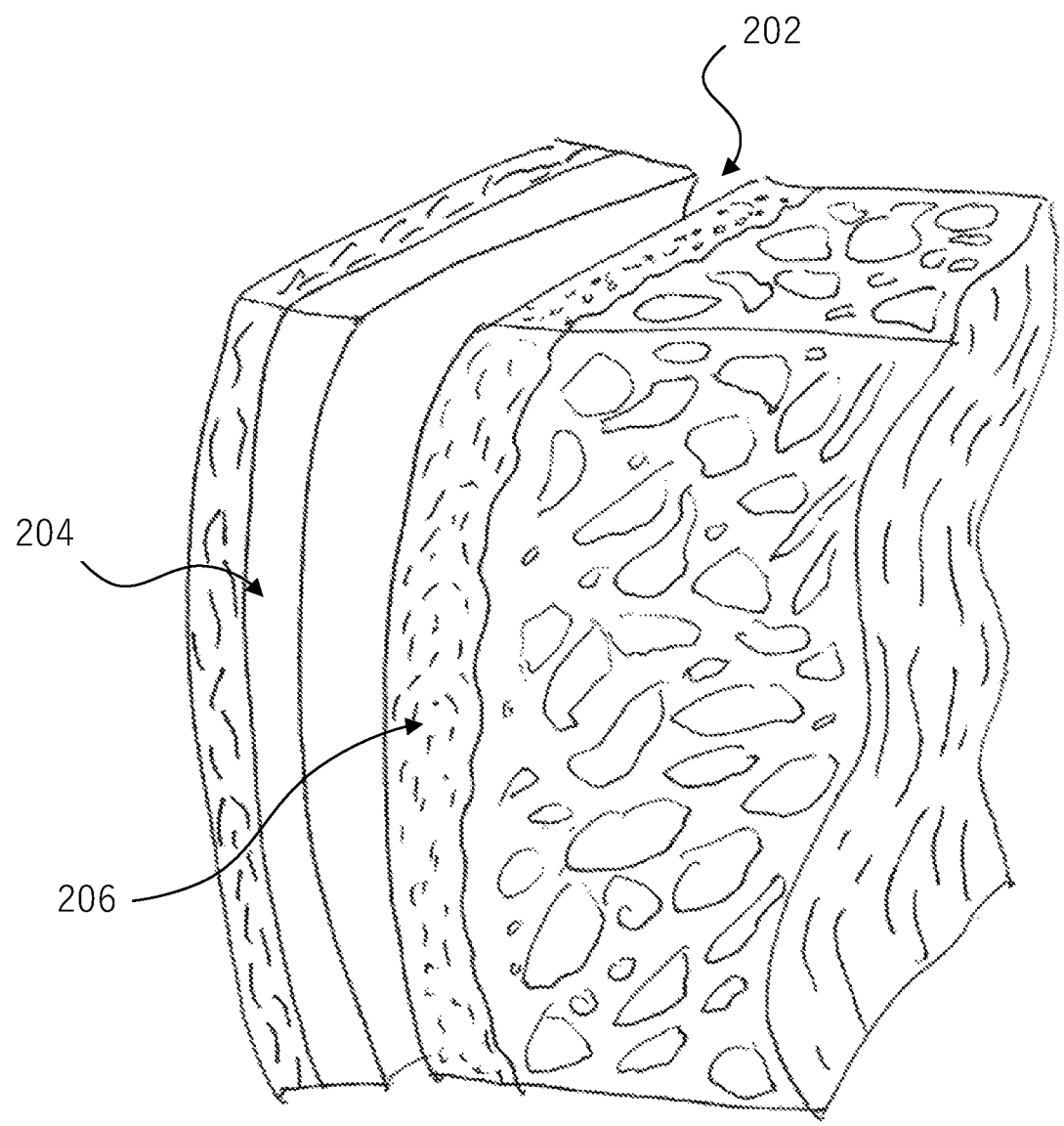
FIG. 12C illustrates a detailed view of the heart including the exterior heart wall, the pericardial cavity or space, and the pericardium.

The pericardium is a membrane that surrounds and protects the heart. FIG. 12C illustrates a detailed view of the heart. FIG. 12C illustrates a portion of an exterior wall of the heart and the pericardium. A pericardial cavity or space 202 exists between the parietal pericardium 204 and the visceral pericardium 206. It is typically desirable to minimize damage to the pericardium during a procedure on the heart in order to ensure that the protective function of the pericardium is not negated. For example, in procedures where a needle is penetrated through an external wall of the heart from a position inside the heart, there is an appreciable risk that the needle will puncture or penetrate the pericardium. The procedures described herein, and specifically those that result in an insufflated space between the heart wall and pericardium, greatly minimize the chance that a needle will puncture or penetrate the pericardium when delivered from inside the heart. In addition, it may be preferred to position one or more heart implants, such as heart anchors described herein, within the pericardium to ensure that the pericardium covers and conceals the heart implants and/or protects internal organs from contact with the heart implants. The procedures described herein enable a heart implant to be easily positioned on an external wall of the heart and within the pericardium.

Accessing the pericaridal space, or insufflation of the pericardial space, from the right atrial appendage may be preferable for several reasons. For example, delivery of a catheter into the left atrial appendage and/or insertion of a needle through the left atrial appendage may increase the chance of clotting of the blood and the negative effects associated therewith. In addition, the right atrial appendage is smaller than the left atrial appendage, which may be ideal for smaller catheter devices, such as the delivery catheter described herein. In addition, the right ventricle is typically lower pressure than the left ventricle, which may enable the needle to penetrate through the right atrial appendage without risking excessive bleeding or other complications. The right atrial appendage is also located in an area where there is minimal concern with contacting or penetrating other tissue with the needle that is penetrated across the heart wall.

While right atrial appendage access may be preferred in many instances, other access sites within the right atrium, left atrium, or right or left ventricles may be selected to access the pericardial space. For example, in some instances a patient may have a pacing lead in or near the right atrial appendage, which may render the right atrial appendage unusable for pericardial space access. In such instances, a nearby site within the right atrium may be selected to access the pericardial space. In other instances, other areas of the right atrium, or another chamber of the heart, may be selected to provide access to the pericardial space. For ease in describing the embodiments herein, the description will generally be directed to accessing the pericardial space from the right atrial appendage. It should be recognized, however, that other access sites in the right atrium, or another heart chamber. may be selected and that the procedure described herein may be employed at any of the selected access sites. As such, the terms "access site", "right atrium", "heart chamber", and the like may be substituted in the description and/or claims without changing the scope of focus of the description and claims.

In specific embodiments, insufflating the pericardial space from the right atrial appendage may create separation between the heart wall and pericardium at or near the left ventricular wall and/or near the heart apex. These locations may be ideal for minimally invasive procedures that are designed to reduce a volume of the left ventricle. In particular, insufflating a space adjacent to the left ventricular wall and/or heart apex may be ideal for procedures in which a heart anchor is positioned on the left ventricular wall and an opposing anchor is positioned on the septal wall or on a right ventricular wall near the apex. The insufflated space may enable a needle to penetrate the left ventricular wall without penetrating through the pericardium. In some embodiments, the insufflated space may enable the heart anchor to be positioned on the left ventricular wall without contacting or engaging the pericardium. As such, the pericardium may remain intact and undamaged during penetration of the heart wall and/or during delivery of the heart anchor to the left ventricular wall.

In some embodiments, a small incision may be made in the pericardium during positioning of the heart anchor on the left ventricular wall. In such embodiments, the insufflated space may aid in creating a separation between the heart wall and pericardium that enables a physician to easily place a heart anchor on the ventricular wall with minimal damage or complications to the pericardium. In such instances, the pericardium may cover and protect the ventricular wall and heart anchors after the procedure is performed.

To access or insufflate a space between the heart wall and pericardium from the access site (e.g., the right atrial appendage), a catheter, cannula, or other device may be positioned in the right atrium or heart chamber at the access site. A distal end of the catheter, cannula, or other device may be inserted within tissue at the access site to anchor the catheter, cannula, or other device to the tissue. In a specific embodiment, a distal end of the catheter, cannula, or other device may include a screw member or tip that is rotated into the tissue at the access site to anchor the catheter, cannula, or other device into the tissue. The distal end of the catheter, cannula, or other device (e.g., the screw tip) may then be retracted to invert or invaginate the tissue at the access site and thereby form a funnel shaped tissue area. Stated differently, inverting or invaginating the tissue at the access site may create a little pocket or recess at the access site. In other embodiments, the distal end of the catheter, cannula, or other device may include other tissue engaging features, such as a needle, a soft-tipped wire, a balloon, a suction device, a barb, a specialized catheter, and the like. The tissue engaging feature may be configured to engage and anchor within tissue at the access site and/or may be retractable to invaginate the tissue at the access site. As briefly mentioned above, for convenience in describing the embodiments herein, the disclosure will refer to the tissue penetrating device as a screw member or screw tip. It should be realized, however, that the term "screw tip" as used in the description or claims may be replaced with tissue engaging feature, or with any of the specific tissue engaging features described in this paragraph.

A needle or other tissue penetrating device may be inserted through the pocket or recess at the access site that is formed by invaginating the tissue. The needle or tissue penetrating device may be inserted entirely through the tissue at the access site without puncturing the pericardium. The invaginated tissue, and the pocket or recess that is formed thereby, may enable the needle or tissue penetrating device to fully penetrate the heart tissue without risking puncture or penetration of the pericardium.

The needle or tissue penetrating device is penetrated through the tissue at the access site so that a distal end of the needle is positioned in a space between the pericardium and an external wall of the heart. A device may then be inserted into the pericardial space to perform a therapeutic intervention or procedure. In a specific embodiment, the needle or tissue penetrating device may be used to insufflate the area surrounding the heart. For example, a gas or fluid may be delivered from the needle or tissue penetrating device into the area surrounding the heart. The delivered gas or fluid may insufflate the area surrounding the heart and thereby create a space between the pericardium and the heart wall.

In some embodiments, the needle/tissue penetrating device may be positioned inside the catheter, cannula, or other device. In such embodiments, the needle/tissue penetrating device may be axially moveable relative to the catheter, cannula, or other device so that a physician is able to extend and retract the needle/tissue penetrating device relative to the catheter, cannula, or other device. In some instances, the screw tip could be hollow so that the insufflation gas or fluid is deliverable through the screw tip and into the space between the heart wall and pericardium.

Having described several aspects of the embodiments generally, additional aspects and details of the insufflation device, and the methods involving the insufflation device, will be evident with reference to the description of the several drawings provided herein below.

Exemplary Catheters

According to one embodiment, a device for anchoring into tissue at an access site (hereinafter right atrial appendage) and/or accessing or insufflating a space between the heart wall and pericardium (hereinafter pericardial space) may include three concentrically positioned components. Specifically, the device may include a delivery catheter, an anchoring member, and a tissue penetrating member. The anchoring member may also be referred to as an inner catheter. The inner catheter may be concentrically positioned within the delivery catheter. The tissue penetrating member may also be referred to as a needle. The needle may be concentrically positioned within the inner catheter. In some instances, the inner catheter may be configured to penetrate into or through heart tissue such that a separate needle component may not be required. The inner catheter may be axially slidable relative to the delivery catheter, which may allow the inner catheter to be extended distally of the delivery catheter and to be retracted within the delivery catheter. Similarly, the needle may be axially slidable relative to the inner catheter, which may allow the needle to be extended distally of the inner catheter and/or delivery catheter and to be retracted within the inner catheter.

The delivery catheter may include a conically or funnel shaped distal end. The conically shaped distal end may facilitate in retracting the heart tissue within the delivery catheter during invagination of the heart tissue. The inner catheter may include a coil or screw tip that enables the inner catheter to be anchored into the heart tissue. The device may also include a handle that allows a physician or operator to manipulate the delivery catheter, inner catheter, and/or needle during a procedure. The handle may include one or more gas or fluid ports that provide gas/fluid access to the distal end of the device for insufflating the pericardial space.

Figure 2:
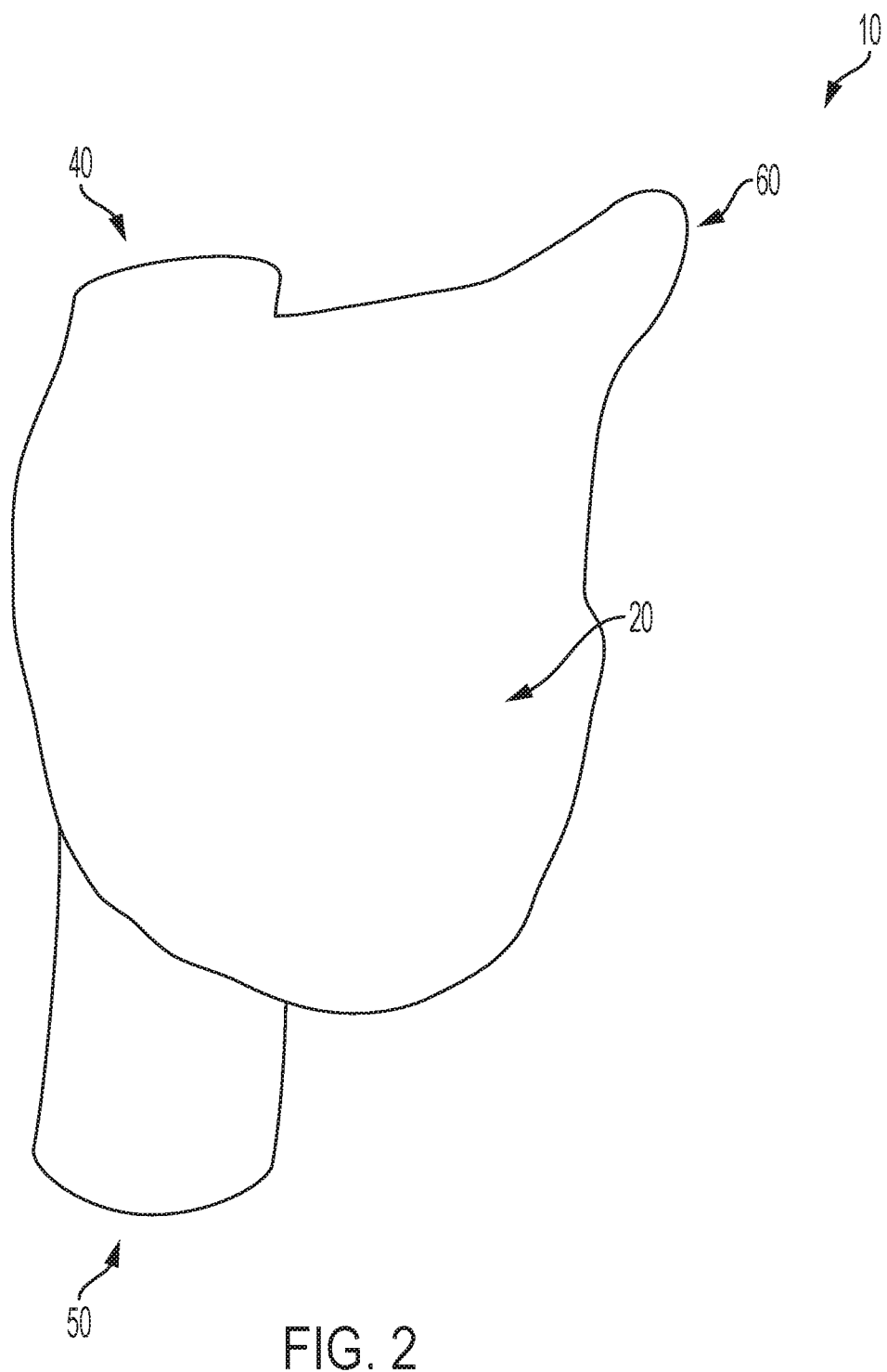
FIG. 2 illustrates the right atrial appendage and right atrium of the heart.

Referring to FIG. 1, illustrated is a simplified drawing of the heart 10 showing the right atrium 20, the aorta 30, the superior vena cava 40, the inferior vena cava 50, and the right atrial appendage 60. For convenience in illustrating these features, other features of the heart 10 have been omitted. In addition, the features illustrated in FIG. 1 are not drawn to scale. FIG. 1 illustrates an access to the right atrium 20 from the femoral and jugular veins. Specifically, to access the right atrium 20, a catheter may be inserted into the jugular vein and then guided through the superior vena cava 40 into the right atrium 20. Alternatively, the catheter can be inserted into the femoral vein and then guided through the inferior vena cava 50 into the right atrium 20. From the right atrium, the catheter can be steered to an access site, such as into the right atrial appendage 60, so that a distal end of the catheter is positioned at the access site. FIG. 2 illustrates the right atrial appendage 60 and the right atrium 20 of the heart 10. The right atrial appendage 60 lies over the aortic root and parallel to the pericardial surface.

Figure 3:
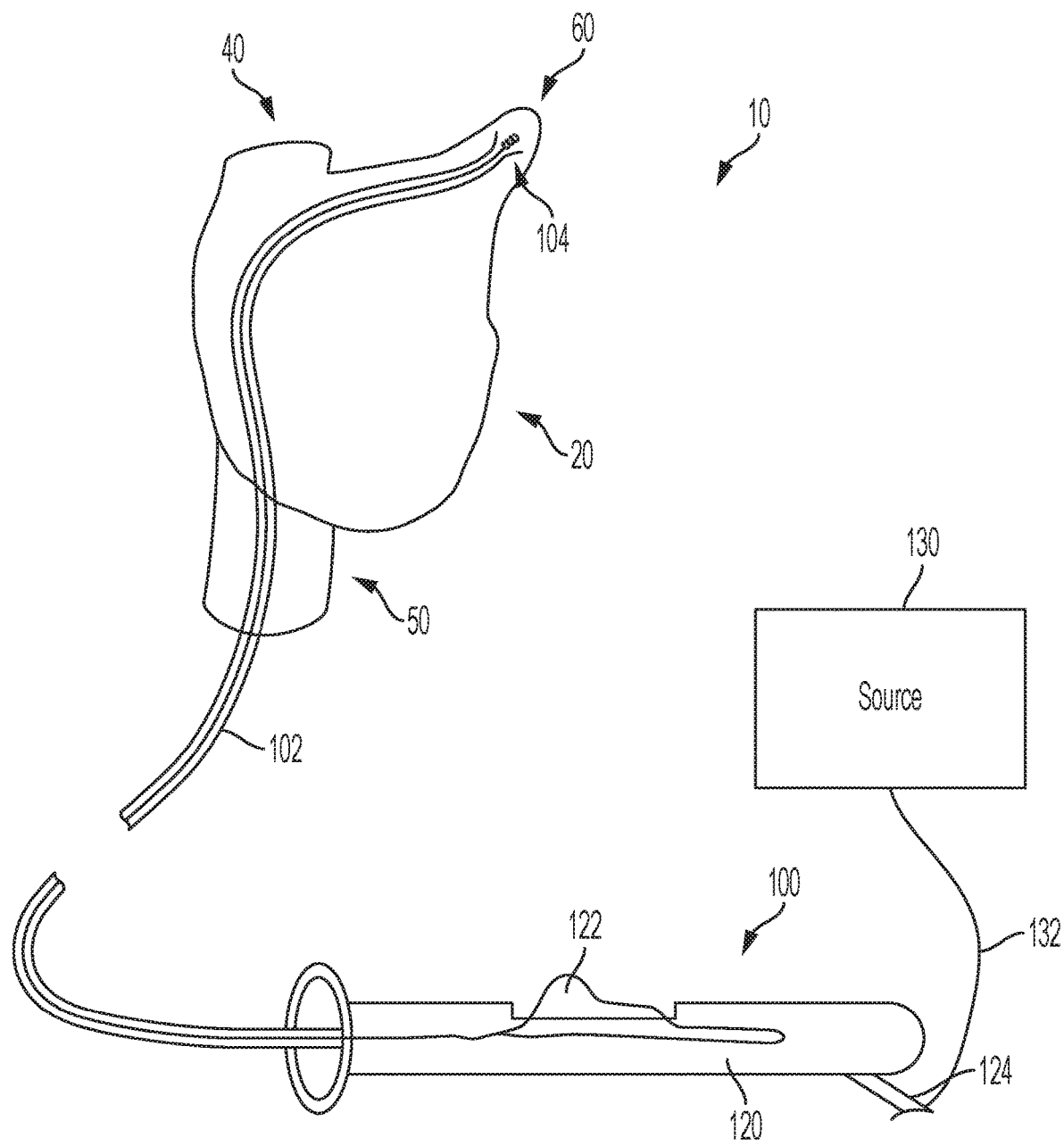
FIG. 3 illustrates the distal end of a delivery catheter positioned in the right atrial appendage of the heart.

FIG. 3 illustrates the distal end 104 of a delivery catheter 100 positioned in the right atrial appendage 60 of the heart 10. The delivery catheter 100 has been inserted through the femoral vein (not shown) and through the inferior vena cava 50 into the right atrium 20. The distal end 104 of the delivery catheter 100 has been guided or steered into the right atrial appendage 60. Although not shown, in other embodiments, the delivery catheter 100 may be inserted through the jugular vein (not shown) and through the superior venal cava 40 into the right atrium 20 of the heart 10. With the distal end 104 of the delivery catheter 100 positioned in the right atrial appendage 60, the delivery catheter 100 may be used to access the pericardial space in order to insufflate the pericardial space or to perform one or more other therapeutic procedures, such as those described herein. The delivery catheter 100 includes an elongate body 102 that is insertable through the vasculature so that the distal end 104 of the delivery catheter 100 is positionable in a right atrial appendage 60. The catheter diameter can range from 5 Fr to 20 Fr depending on the access and the components. To position the distal end 104 within the right atrial appendage 60, the distal end 104 of the delivery catheter 100 may be steerable.

A handle mechanism 120 is positioned on the proximal end of the elongate body 102. The handle mechanism 120 may be operable to steer the distal end 104 of delivery catheter 100 and/or to manipulate the anchoring member (e.g., screw tip) and/or tissue penetrating member (e.g., needle). In some embodiments, a gas or fluid source 130 is coupleable with an access port 124 of the handle mechanism 120. In a specific embodiment, the gas or fluid source provides gas or fluid to the delivery catheter, which may be delivered to the pericardial space through the access port 124. In other embodiments, a device (catheter, camera, heart implant, and the like) may be delivered through the access port 124 to perform one or more therapeutic interventions or procedures described herein. For example, a camera and optical fiber may be inserted through the access port 124 and into the pericardial space to view the exterior of the heart wall. In other embodiments, a lead may be positioned through the access port 124 into the pericardial space to pace the heart and/or monitor heart pressure or pulse. A specialized catheter could be inserted through the access port 124 to suction bleeding, drain pericardial fluid, perform an epicardial biopsy, map a portion of the heart, and the like.

As described in greater detail herein, the anchoring member is extendible from a lumen of the elongate body and into a heart wall of the right atrial appendage 60 to secure the distal end 104 of the elongate body 102 within the right atrial appendage 60. Gas or fluid may be deliverable from the gas or fluid source 130, through the access port 124, and into the pericardial space via a penetration in the heart wall of the right atrial appendage 60. The gas or fluid that is delivered into the pericardial space insufflates the pericardial space. The tissue penetrating member is typically positioned within the lumen of the elongate body and is configured to penetrate the heart wall of the right atrial appendage 60 and thereby provide access to the pericardial space around the heart.

Figure 9:
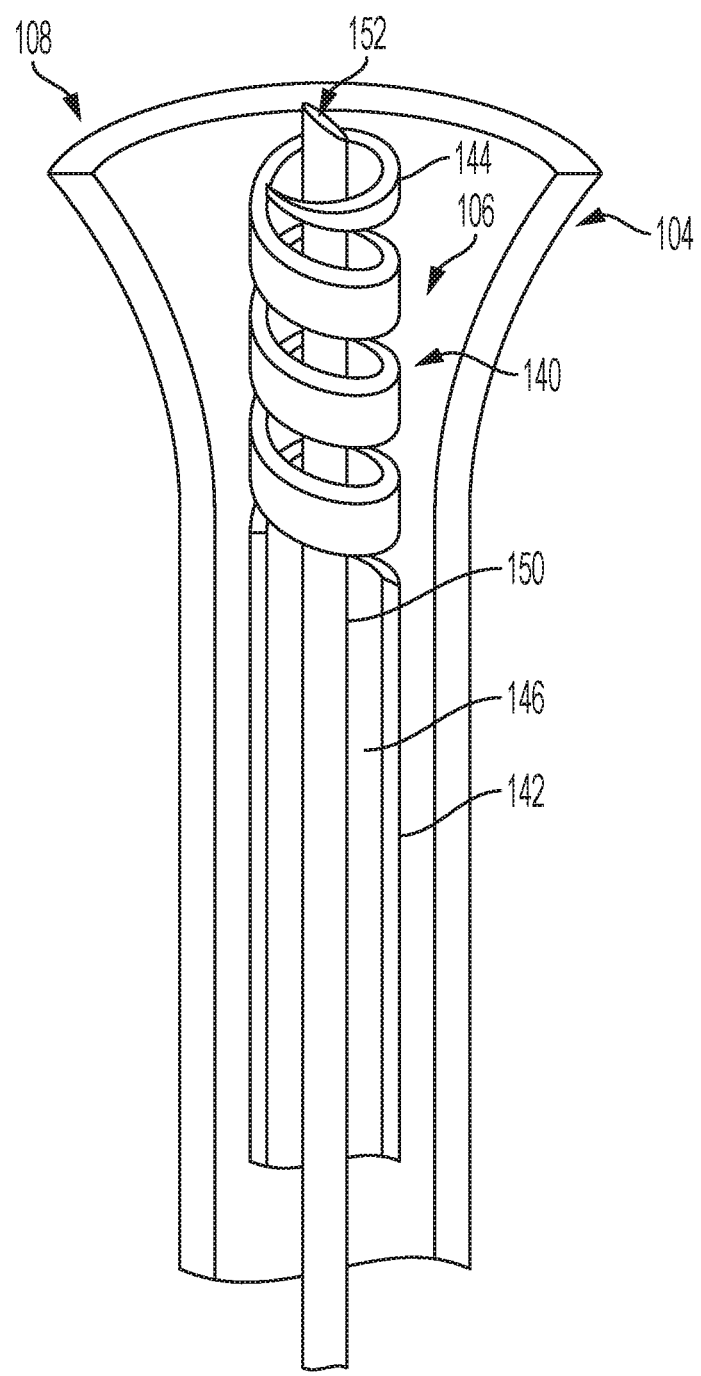
FIG. 9 illustrates a detailed view of the delivery catheter including an anchoring member and tissue penetrating member.

Referring now to FIG. 9, illustrated is a detailed view of the distal end 104 of the delivery catheter 100. The distal end 104 of the delivery catheter 100 may have a curved configuration that corresponds to a geometry of the extension of the right atrial appendage 60 from the right atrium 20. The curved configuration of the distal end 104 of the delivery catheter 100 may facilitate in inserting the distal end 104 into the right atrial appendage 60 or elsewhere at a selected access site. Positioned within the delivery catheter 100 is an anchoring member or inner catheter 140 (hereinafter inner catheter 140) and a tissue penetrating member or needle 150 (hereinafter needle 150). It should be recognized that the needle 150 is representative of any perforating device (e.g., laser or RF energy device) and is not limited to a needle 150 in the description. In addition, although FIG. 9 illustrates both the inner catheter 140 and needle 150, it should be realized that in some embodiments one of these components may be excluded. For example, in some embodiments the inner catheter 140 may be configured to function in a manner similar to the needle 150 so that the use of a separate needle 150 is not required. More specifically, the inner catheter 140 may be configured to penetrate through the tissue of the heart and/or to deliver an insufflation gas or fluid to the pericardial space. In other embodiments, the needle 150 may be configured to function in a manner similar to the inner catheter 140 so that use of the inner catheter 140 is not required. More specifically, the needle 150 may be configured to anchor into the heart tissue and/or to retract the heart tissue into the distal end 104 of the delivery catheter 100.

In the embodiment illustrated in FIG. 9, the needle 150 is concentrically positioned within the inner catheter 140, which is in turn concentrically positioned within the delivery catheter 100. The delivery catheter 100 includes a lumen 106 that extends between a proximal end and the distal end 104 of the elongate body 102. The inner catheter 140 is positioned within the lumen 106 so that the inner catheter 140 is axially slidable within the lumen 106. The axial slidability of the inner catheter 140 allows the inner catheter 140 to be extended distally of the distal end 104 of the catheter 100 or to be retracted within the lumen 106 of the catheter. In some embodiments, the distal end 104 of the delivery catheter 100 may be funnel or conically shaped 108. In some embodiments, the distal end 104 may have a permanently funnel or conically shaped configuration. In other embodiments, the distal end 104 may be reconfigurable between a relatively straight configuration, in which the distal end 104 has a cylindrical shape that corresponds to a shape of the elongate body 102, and a funnel or conically shaped configuration in which the distal end 104 is conically shaped 108. The conically shaped 108 distal end may aid in retraction of the inner catheter 140 within the lumen 106 of the delivery catheter 100 during invagination of the right atrial appendage 60.

The inner catheter 140 is configured to anchor or secure within a heart wall of the right atrial appendage 60. Anchoring the inner catheter 140 to the heart wall secures the distal end 104 of the delivery catheter 100 within the right atrial appendage 60. To anchor the inner catheter within the heart wall, the inner catheter 140 includes a screw tip or member 144 (hereinafter screw tip 144) that is positioned on a distal end of a tube or catheter body 142. The screw tip 144 is configured to screw into the heart wall of the right atrial appendage 60. In some instances, the screw tip 144 may be formed from the catheter body 142 itself. For example, the distal end of the catheter body 142 may have a threaded or helical configuration with a sharp tissue penetrating tip. In other instances, the screw tip 144 may be a separate component that is coupled with the catheter body 142. The screw tip 144 and/or catheter body 142 may be hollow, which may allow the screw tip 144 to be inserted or threaded into the heart tissue and deliver or inject an insufflation gas/fluid, or other material, into the heart tissue. Alternatively, the insufflation gas/fluid, or other materials, may be injected into the heart tissue through a central lumen 146 of the catheter body 142. In such instances, the needle 150 may be omitted from the catheter and catheter system.

As briefly described herein, the inner catheter 140 is retractable within the lumen 106 of the elongate body 102. The screw tip 144 is sufficiently strong so that when the distal end of the inner catheter 140 is anchored within the heart tissue, retraction of the inner catheter 140 within the lumen 106 pulls the heart tissue into the lumen 106 of the elongate body 102. The conically shaped 108 distal end of the delivery catheter 100 aids in retraction of the heart tissue within the lumen 106 by eliminating sharp edges or corners that would contact the heart tissue and resist insertion of the heart tissue within the lumen 106.

The needle 150 is positioned within the lumen 146 of the inner catheter's catheter body 142 so that the needle 150 is axially slidable within the lumen 146. The axial slidability of the needle 150 allows the needle 150 to be extended distally of the screw tip 144 and to be retracted within the lumen 146 of the catheter body 142. The needle 150 is configured to penetrate the heart wall of the right atrial appendage 60 to provide gas or fluid access to the pericardial space of the heart 10. In some instances, the needle 150 may be extended distally of both the screw tip 144 and the distal end 104 of the delivery catheter 100 in penetrating the heart wall. In other embodiments, the needle 150 may be extended distally of the screw tip 144, but may remain within the lumen 106 of the elongate body 102 so that the needle 150 does not extend beyond a distal tip of the delivery catheter 100. The latter procedure may be preferable when the needle 150 is used to penetrate the heart wall after the right atrial appendage 60 is pulled or retracted within the lumen 106 of the elongate body 102. In such instances, the needle 150 does not need to extend beyond the distal tip of the delivery catheter in order to fully penetrate the heart wall. Rather, the needle 150 may remain within the lumen 106 of the elongate body, which may aid in ensuring that the needle 150 does not penetrate or puncture the pericardium.

While the tissue penetrating device is illustrated as a needle 150 in FIG. 9, it should be realized that various other tissue penetrating means may be substituted for the needle. For example, the tissue penetrating device may be an electrical device, an RF device, and the like that is configured to penetrate tissue. As such, any means of penetrating tissue may be used in place of the needle 150. The needle 150, or other tissue penetrating device, is typically hollow 152 and is fluidly coupled with a gas or fluid source (e.g., source 130 of FIG. 3). The gas or fluid is deliverable through the hollow needle and into the pericardial space to insufflate the pericardial space.

Referring now to FIGS. 10A-B illustrated is an embodiment of the inner catheter 140 and needle 150. The screw tip 144 and needle 150 are illustrated in detail in FIG. 10B, which specifically shows the screw tip 144 being formed from the catheter body 142. The needle 150 is slidably positioned within the lumen 146 of the catheter body 142. A handle mechanism 160 is positioned on a proximal end of the catheter body 142. In some embodiments, the handle mechanism 160 may also be positioned on, and coupled with, a proximal end of the delivery catheter 100. The handle mechanism 160 includes a first member 162 that is operably coupled with the inner catheter 140 and a second member 164 that is operably coupled with the needle 150. A user actuation of the first member 162 causes the inner catheter 140 to extend distally of the delivery catheter's elongate body 102 and anchor within the heart wall of the right atrial appendage 60. For example, the first member 162 may be a rotatable knob that a user may grasp and rotate to rotate the screw tip 144. Rotation of the screw tip 144 may screw or thread the screw tip 144 into the heart tissue of the right atrial appendage 60, which may pull the inner catheter 140 distally of the delivery catheter's distal end 104. In some instances, the user may push axially on the handle mechanism 160 and simultaneously rotate the knob to cause the screw tip 144 to extend distally of the delivery catheter's elongate body 102 and anchor within the heart tissue.

A user actuation of the second member 164 may cause the needle 150 to penetrate the heart wall of the right atrial appendage 60. For example, the second member 164 may be a slidable button or lever that is coupled with the needle 150 in a manner that causes the needle to extend and retract relative to the inner catheter 140. In such instances, the second member 164 may be slid forward to cause the needle 150 to penetrate the heart wall of the right atrial appendage 60. In other embodiments, the second member 164 may be coupled with the inner catheter 140 in a manner that causes the inner catheter 140 to move axially about a stationary needle 150. In such instances, the second member 164 may be slid backward to cause the inner catheter 140 and anchored heart tissue to move backward relative to the stationary needle 150 and thereby penetrate the heart wall of the right atrial appendage 60 with the needle 150. The handle mechanism 160 may be insertable through the lumen 106 of the delivery catheter's elongate body 102, or may be operably coupled with the delivery catheter 100 as desired.

The handle mechanism 160 may also include a gas or fluid access port 166 that is fluidly coupled with the distal end of the inner catheter 140 or the needle 150. The gas or fluid access port 166 is fluidly coupled with the inner catheter 140 or the needle 150 via tubing that extends from the access port 166 to the respective component. The gas or fluid access port 166 is configured to receive an insufflation gas or fluid from a fluid source (e.g., source 130 of FIG. 3) by allowing the fluid source to be attached or coupled with the access port 166. The gas or fluid may be injected through the access port 166, through the tubing (not shown), and through the hollow needle 152 or hollow screw tip 144 into the pericardial space to insufflate the pericardial space.

Figure 11:
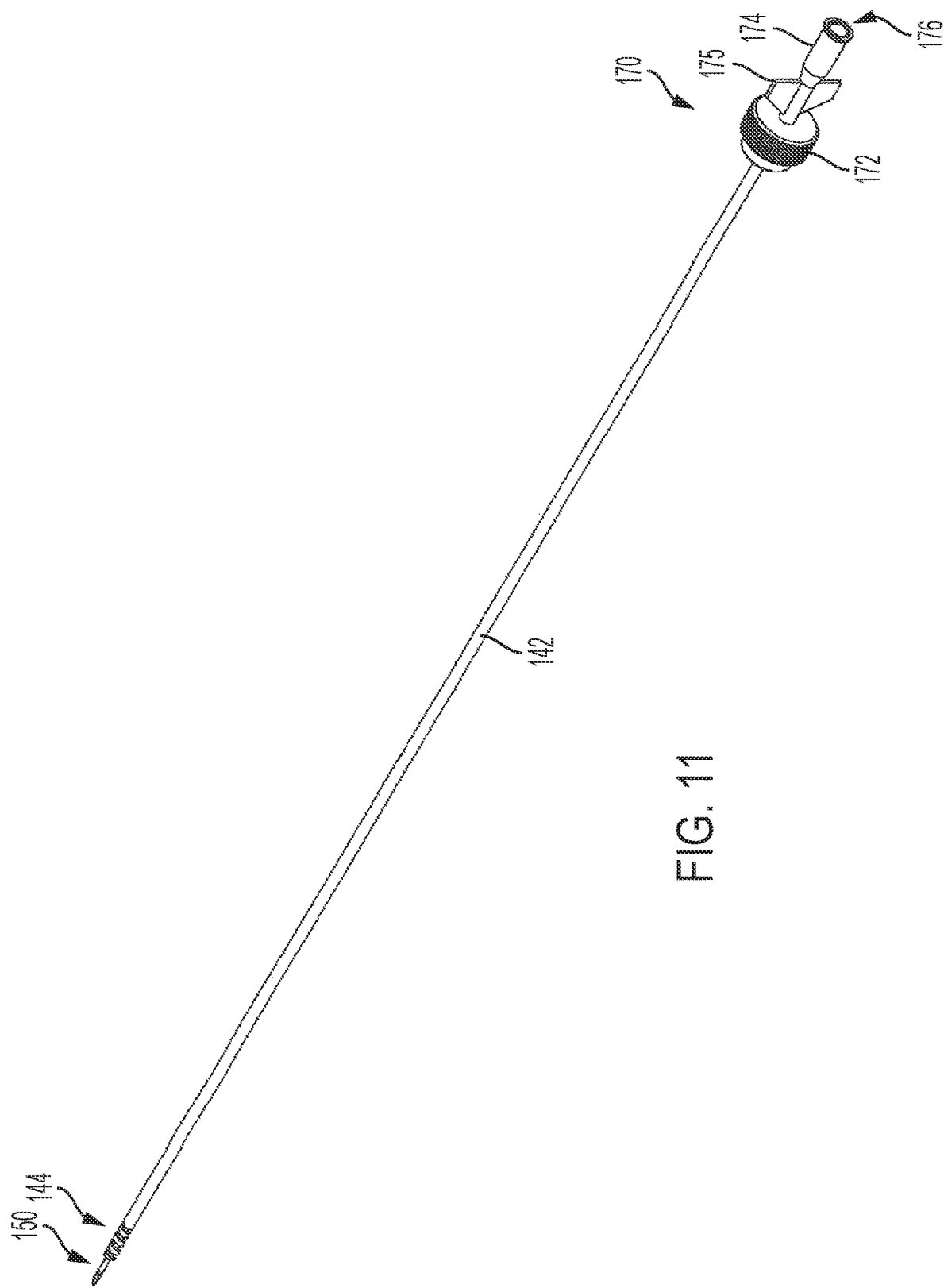
FIG. 11 illustrates another embodiment of the anchoring member and tissue penetrating member.

Referring to FIG. 11, illustrated is another embodiment of the inner catheter 140 and needle 150. Specifically, FIG. 11 illustrate another handle mechanism 170 that is coupled with the inner catheter 140 and needle 150. The handle mechanism 170 may be particularly useful with a delivery catheter in which it is desired to remove the inner catheter 140 and/or needle 150 from the lumen 106 of the delivery catheter. In such instances, it may be desirable to have an inner catheter 140 and/or needle 150 that is separate from the delivery catheter 100.

The handle mechanism 170 includes a first member 172 that is coupled with the inner catheter 140. The first member 172 may be a rotatable knob that is able to effect a rotation of the screw tip 144 upon a user operation of the knob. The rotation of the screw tip 144 may cause the screw tip 144 to anchor into the heart tissue of the right atrial appendage 60. The first member 172 may also be grasped and moved axially in a proximal and distal direction within the lumen 106 of the delivery catheter 100 to cause the screw tip 144 to extend distally from the delivery catheter's distal end 104 or to retract the screw tip 144 and any anchored heart tissue within the lumen 106.

The handle mechanism 170 also includes a second member 174 that is coupled with the needle 150. The second member 174 and needle 150 are axially slidable within the lumen 146 of the catheter body 142 in order to allow the needle 150 to be extended distally of the screw tip 144 and to be retracted proximally within the catheter body's lumen 146. The second member 174 may include a pair of ribs 175 that aid in sliding or moving the needle 150 axially within the catheter body 142. A gas or fluid access port 176 may be formed on the distal end of the second member 174. The access port 176 may be coupled with a gas or fluid source as described herein, or as known in the art.

Exemplary Methods

Figure 4:
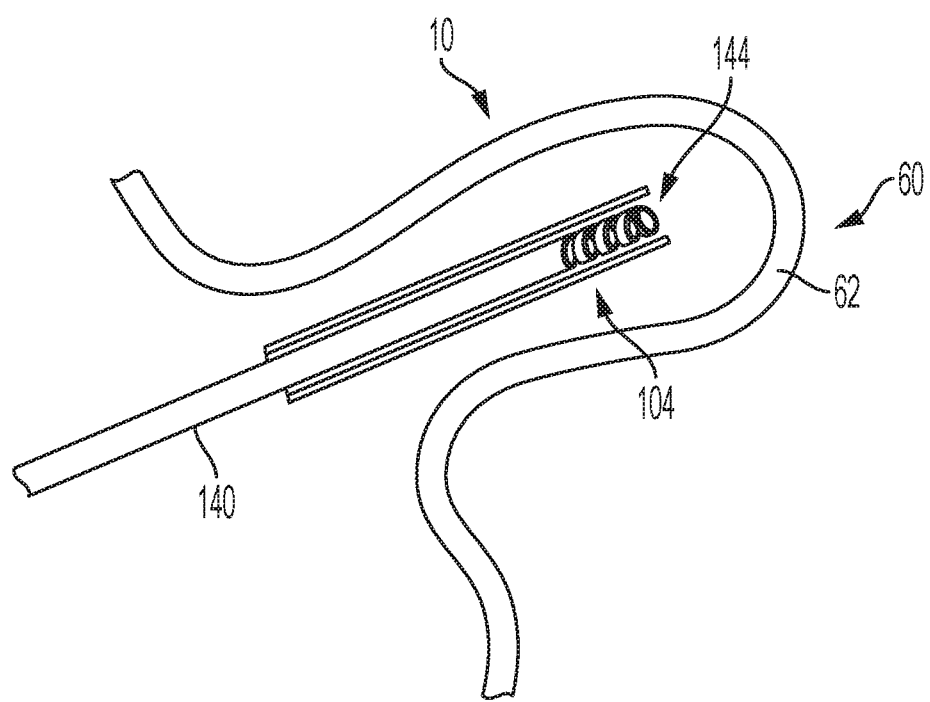
FIG. 4 illustrates a detailed view of the right atrial appendage with the distal end of the delivery catheter positioned in the right atrial appendage.
Figure 5:
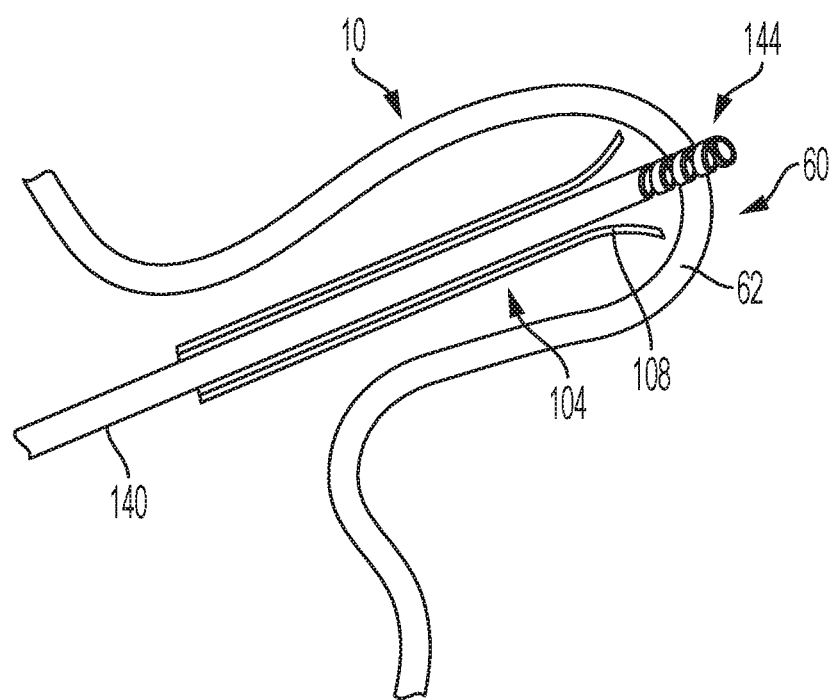
FIG. 5 illustrates a screw member or screw tip of the delivery catheter advanced into the right atrial appendage.

Referring to FIGS. 4-8, illustrated is a process for accessing a pericardial space to perform a therapeutic intervention, such as insufflating the pericardial space, and/or for anchoring the delivery catheter 100 at the access site (e.g., within the right atrial appendage 60) to perform the therapeutic intervention. In FIG. 4, the distal end 140 of the delivery catheter 100 has been guided, steered, or delivered into the right atrium 20 of the heart 10, and more specifically, the delivery catheter 100 has been steered so that a distal end of the catheter 100 is positioned adjacent an access site in the right atrium 20. In a specific embodiment, the right atrial appendage 60 has been accessed so that the distal end 104 of the delivery catheter 100 is positioned in the right atrial appendage 60. For ease in describing the remainder of the process, the access site will be referred to as the right atrial appendage 60. With the distal end 104 of the delivery catheter 100 positioned in the right atrial appendage 60, the distal end 104 of the delivery catheter 100 may be anchored in a heart wall 62 of the right atrial appendage 60. To anchor the distal end 104 of the delivery catheter 100 in the heart wall 62, the screw tip 144 may be extended distally of the delivery catheter 100. More commonly, the screw tip 144 is rotated, via a component or member of a handle mechanism, to cause the screw tip 144 to screw, thread, or otherwise penetrate the heart wall 62 in the right atrial appendage 60. FIG. 5 illustrates the screw tip 144 extended distally of the delivery catheter 100 and anchored into the heart wall 62 of the right atrial appendage 60.

Figure 6:
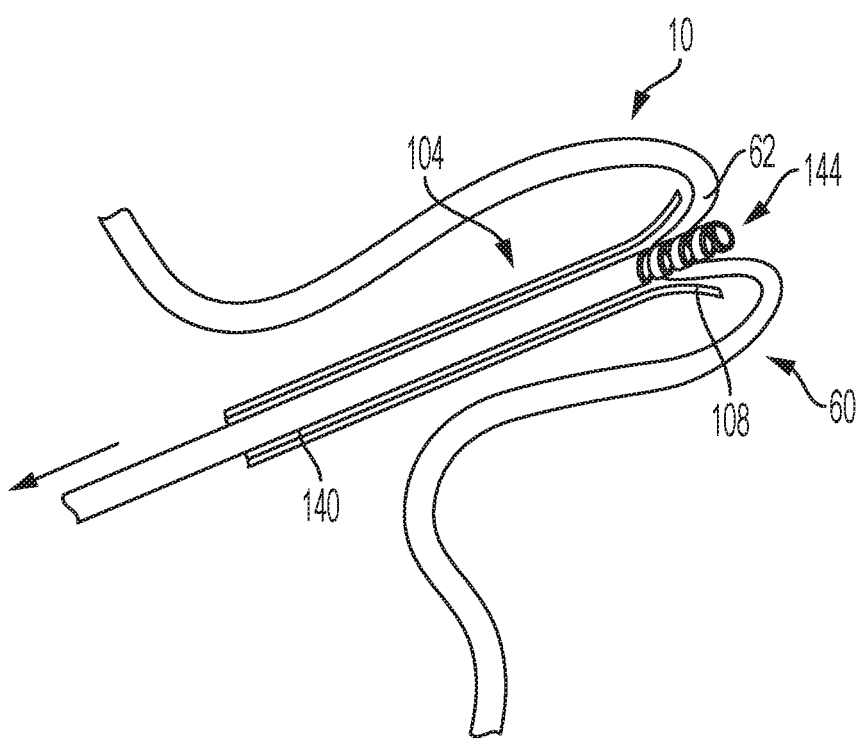
FIG. 6 illustrates the screw tip retracted within the delivery catheter to invaginate the tissue of the right atrial appendage.

In some embodiments, the distal end 104 of the delivery catheter 100 may be expanded so that the distal tip of the delivery catheter 100 assumes a funnel or conical shape. In FIG. 6, the screw tip 144 is retracted within the lumen 106 of the delivery catheter 100, which causes the anchored portion of the heart wall 62 to be pulled inward relative to the right atrial appendage 60 and typically into the conically shaped distal end 104 of the delivery catheter 100. Pulling the heart wall 62 inward causes the heart wall 62 to be inverted or invaginated, thereby forming a pocket or recess in the right atrial appendage 60 and separating an exterior surface of the inverted heart wall from contact with parietal pericardial tissue. Stated differently, inverting or otherwise manipulating the heart wall creates a "space" in which the heart wall ceases to have contact with parietal pericardial surfaces. The screw tip 144 may be retracted so that a distal tip of the screw tip is positioned proximally of the distal tip of the delivery catheter 100. In other embodiments, the screw tip 144 may be retracted so that the screw tip 144 is not fully retracted within the lumen 106 such that a portion of the screw tip 144 remains extended from the distal tip of the delivery catheter 100.

In some embodiments, the distal end 104 of the delivery catheter 100 may not be expanded 108 into the conical shape. Rather, the distal end 104 of the delivery catheter 100 may have a cylindrical shape and profile that matches the cylindrical shape and profile of the elongate body 102. In addition, in some embodiments, the screw tip 144 may not be retracted relative to the delivery catheter 100. In such embodiments, the screw tip 144 may remain anchored in the heart wall 62 as illustrated in FIG. 5. The other procedures described herein may be performed with the screw tip 144 anchored in the heart wall 62 in an non-retracted state.

Figure 7:
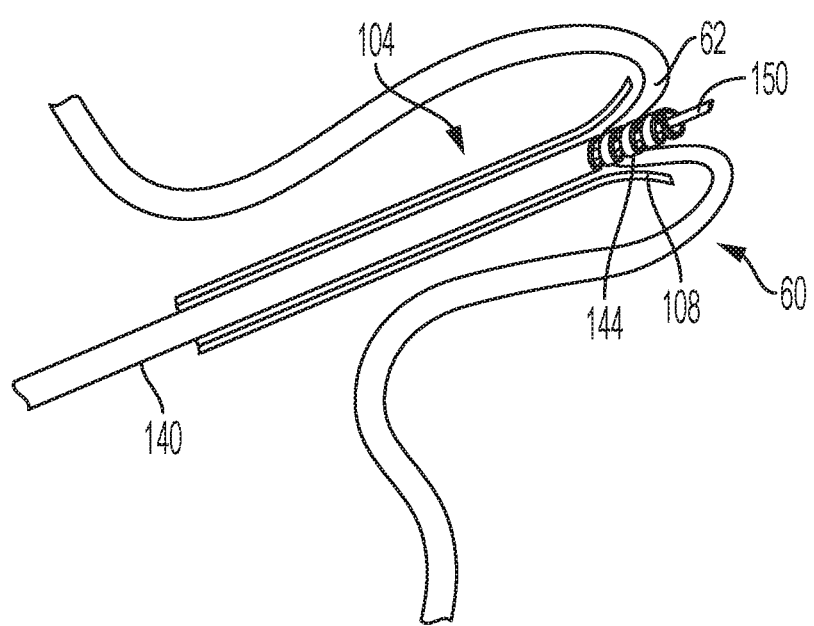
FIG. 7 illustrates a needle advanced through the tissue of the right atrial appendage so that the needle is positioned outside the heart and within the pericardial space.
Figure 8:
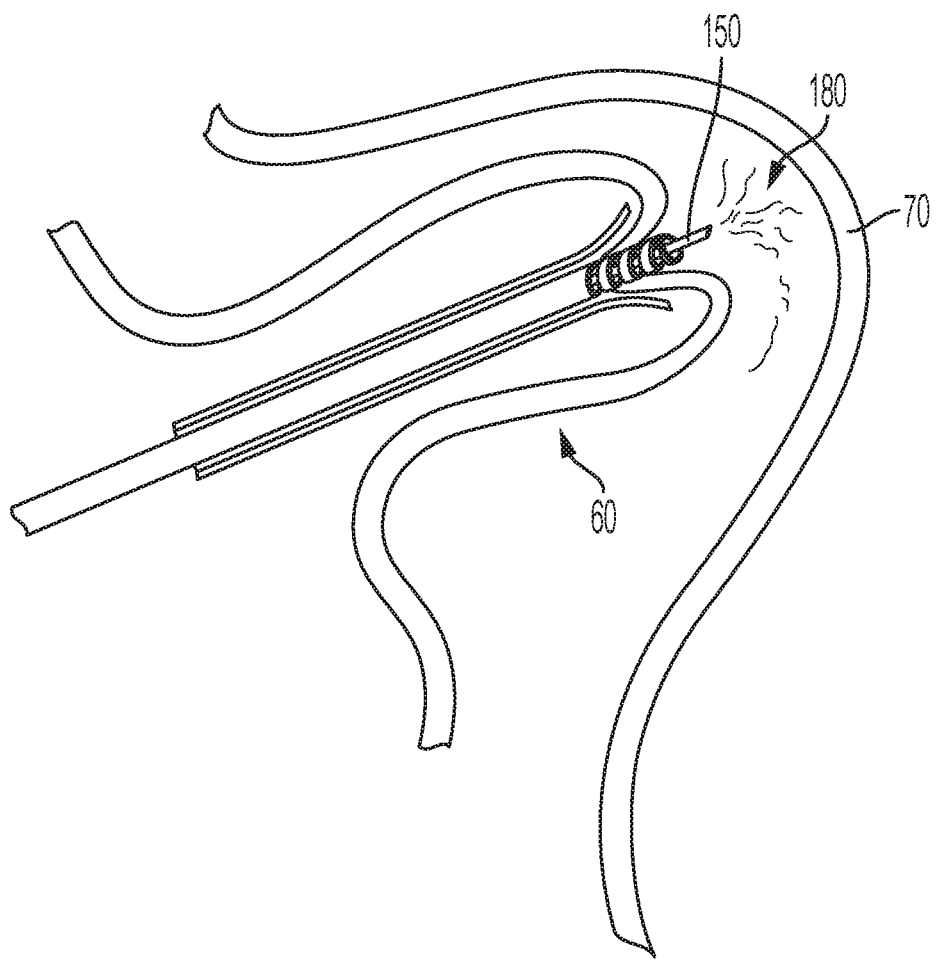
FIG. 8 illustrates a gas or fluid being delivered from the needle within the pericardial space to inflate the pericardial space.

In FIG. 7, the heart wall 62 is penetrated to provide access to the pericardial space of the heart. With the heart wall 62 penetrated, the delivery catheter 100 has access to the pericardial space. To penetrate the heart wall 62, the needle 150 (or other tissue penetrating device) is extended distally relative to the inner catheter 140 and through the anchored portion of the heart wall 62. The needle 150 may be extended distally of the screw tip 144 and/or the distal tip of the delivery catheter 100, although in some embodiments this is not required since the anchored portion of the heart wall 62 is typically positioned within the flared end 108 of the delivery catheter 100. In such instances, the needle 150 may be extended through the heart wall 62, but may remain positioned within the lumen 106 of the delivery catheter 100 or within the threads of the screw tip 144.

In some embodiments, the process illustrated in FIG. 7 may not be performed. For example, in instance in which the screw tip 144 (or other tissue penetrating device) is hollow, the screw tip 144 may penetrate through the heart wall 62 so that the distal tip of the screw tip 144 is positioned in the pericardial space. In such instances, the use of the needle 150 may not be required and the therapeutic intervention or procedure may be performed with the catheter 100 or screw tip 144. For example, a gas or fluid may be injected into the pericardial space from the screw tip 144 itself. Alternatively, another procedure may be performed with the screw tip 144 inserted into and/or through the heart wall 62. The heart wall 62 may or may not be invaginated depending on the procedure being performed.

In the embodiment illustrated in FIG. 7, the distal tip of the needle 150 is positioned in the pericardial space or otherwise has access to the pericardial space. The needle 150 is also positioned concentrically within the inner catheter 140. With the needle 150 positioned so that it is accessible to the pericardial space, the therapeutic intervention or procedure may be performed. For example, a gas or fluid 180 may be delivered into the pericardial space to insufflate the pericardial space and thereby form a cavity or create separation between the pericardium 70 and an exterior wall of the heart. In another embodiment, a specialized device (e.g., a catheter, camera, lead, etc.) may be delivered through the penetration in the inverted heart wall to perform the therapeutic intervention in the pericardial space. In the illustrated embodiment, the gas or fluid 180 is delivered into the pericardial space through the lumen 152 of the needle 150. In other embodiments, the gas or fluid 180 may be delivered into the pericardial space through a lumen of the screw tip 144 or other tissue penetrating device.

The gas or fluid 180 that is injected or delivered into the pericardial space may be $CO_2$ gas. This gas may be preferable because it can be easily dissipated within the body cavity. In some embodiments, the pericardium 70 can be expanded via the delivered gas or fluid 180 until the intrapericardial pressure causes hemodynamic compromise. The pressure of the gas or fluid outside the heart can be monitored to ensure no tamponade is happening to the heart itself. Tamponade can be detected with standard hemodynamic monitoring. With the pericardial space insufflated, one or more therapeutic procedure may be performed on or near the heart. The therapeutic procedures that may be performed include monitoring a pressure outside of the heart, positioning a heart implant or instrument exterior to the heart, irrigating an exterior of the heart, suctioning bleeding, and the like. In some embodiments, these therapeutic procedures may be performed without insufflating the pericardial space.

In a specific embodiment, the pericardial space may be insufflated to aid in delivery of a heart implant to one or more walls of the heart. The heart implant may be delivered to one or more wall of the heart in order to reduce a volume of a chamber of the heart. FIGS. 12A and 12B illustrate a series of implants 80 that are implanted in a heart H so as to decrease a cross-section of a left ventricle LV of the heart H. Each implant 80 generally includes a first anchor 82 that is positioned on the septal wall S of the heart H, a second anchor 84 that is positioned on an exterior wall EW of the heart H, and a tension member 86 that couples the anchors together. Tension in the tension member 86 is transferred from the anchors 82, 84 to the septum S and the external wall EW bordering the left ventricle LV so as to bring these structures into engagement, thereby effectively excluding a region of scar tissue ST from the left ventricle. When the second anchor 84 is positioned on the exterior wall EW, the second anchor 84 is disposed within the pericardium rather than being positioned atop and engaging with the pericardium.

The implant 80 may be deployed by penetrating the external wall EW and septum S with a needle or tissue penetrating device (not shown). The external wall EW and/or septum S may be penetrated by a needle or tissue penetrating device (not shown) that is positioned inside the heart, such as within the right ventricle RV or left ventricle LV, or by a needle or tissue penetrating device (not shown) that is inserted from outside the heart. The first anchor 82 and/or the second anchor 84 may be delivered to the septum S or external wall EW via a heart anchor delivery catheter (not shown). Exemplary devices and methods for accessing and penetrating the heart, and for delivering one or more anchors to the heart, are further described in U.S. Pat. No. 8,979,750, issued on Mar. 17, 2015, entitled "Trans-Catheter Ventricular Reconstruction Structures, Methods, and Systems for Treatment of Congestive Heart Failure and other Conditions", and in U.S. application Ser. No. 15/418,152, filed Jan. 27, 2017, entitled "Percutaneous Arterial Access to Position Trans-Myocardial Implant Devices and Methods", the entire disclosures of which are incorporated by reference herein.

While several embodiments and arrangements of various components are described herein, it should be understood that the various components and/or combination of components described in the various embodiments may be modified, rearranged, changed, adjusted, and the like. For example, the arrangement of components in any of the described embodiments may be adjusted or rearranged and/or the various described components may be employed in any of the embodiments in which they are not currently described or employed. As such, it should be realized that the various embodiments are not limited to the specific arrangement and/or component structures described herein.

In addition, it is to be understood that any workable combination of the features and elements disclosed herein is also considered to be disclosed. Additionally, any time a feature is not discussed with regard in an embodiment in this disclosure, a person of skill in the art is hereby put on notice that some embodiments of the invention may implicitly and specifically exclude such features, thereby providing support for negative claim limitations.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A method for performing a therapeutic intervention in a pericardial space of a heart, the method comprising:
   delivering a catheter into a right atrium of the heart;
   steering the catheter within the right atrium so that a distal end of the catheter is positioned adjacent an access site in the right atrium;
   anchoring the distal end of the catheter in a heart wall of the right atrium adjacent the access site including engaging the heart wall with an anchoring member that is disposed within a lumen of the catheter;
   inverting the heart wall at the access site to separate an exterior surface of the inverted heart wall from contact with parietal pericardial tissue;
   penetrating the inverted heart wall at the access site to provide access to the pericardial space of the heart including extending a needle through the inverted heart wall; and
   delivering a device through a penetration in the inverted heart wall to perform the therapeutic intervention in the pericardial space of the heart.

2. The method of claim 1, wherein the anchoring member comprises a rotatable screw, a barb, a hook, a snare, or a suction device.

3. The method of claim 1, further comprising retracting the anchoring member to invert the heart wall of the right atrium at the access site.

4. The method of claim 3, further comprising retracting the anchoring member to pull the heart wall into a conically shaped end of the catheter.

5. The method of claim 1, wherein the device that is delivered through the penetration in the inverted heart wall comprises a catheter, a perforating device, a hollow needle, a heart anchor, a pressure monitor, or a lead.

6. The method of claim 1, wherein the inverted heart wall is penetrated with a perforating device.

7. The method of claim 6, wherein the perforating device comprises a needle, a laser, or a radio frequency energy delivery device.

8. The method of claim 1, wherein the needle is positioned concentrically relative to the anchoring member.

9. The method of claim 1, further comprising delivering gas or fluid into the pericardial space through a lumen of the needle to insufflate the pericardial space.

10. The method of claim 1, further comprising delivering gas or fluid into the pericardial space through a lumen of the anchoring member to insufflate the pericardial space.

11. The method of claim 1, wherein the access site comprises a right atrial appendage.

12. The method of claim 1, wherein the therapeutic intervention comprises: insufflating the pericardial space; monitoring a pressure outside of the heart;

positioning a heart implant or instrument exterior to the heart;
irrigating an exterior of the heart; suctioning bleeding; draining pericardial fluid; performing an epicardial biopsy; mapping a portion of the heart; or pacing the heart.

13. A method comprising:
delivering a catheter into a right atrium of a beating heart;
anchoring a distal end of the catheter in a heart wall of the right atrium;
using the anchored distal end to invert a portion of the heart wall to partially separate an exterior surface of the heart wall from parietal pericardial tissue;
penetrating with a perforating device the inverted portion of the heart wall by extending a needle through the inverted portion of the heart wall to form a penetration; and
delivering a device through the penetration to perform a therapeutic intervention in the pericardial space of the heart.

14. The method of claim 13, wherein the step of anchoring the distal end of the catheter in the portion of the heart wall comprises engaging the portion of the heart wall with an anchoring member disposed within a lumen of the catheter.

15. The method of claim 14, wherein the anchoring member comprises a rotatable screw, a barb, a hook, a snare, or a suction device.

16. The method of claim 14, further comprising retracting the anchoring member to invert the portion of the heart wall.

17. The method of claim 16, further comprising retracting the anchoring member to pull a region of the heart wall into a conically shaped region of the distal end of the catheter.

18. The method of claim 14, further comprising delivering gas or liquid into the pericardial space through a lumen of the anchoring member to insufflate the pericardial space.

19. The method of claim 13, wherein the device delivered through the penetration in the inverted portion of the heart wall comprises a catheter, a perforating device, a hollow needle, a heart anchor, a pressure monitor, or a lead.

20. The method of claim 13, wherein the perforating device comprises a needle, a laser, or a radio frequency energy delivery device.

21. The method of claim 13, wherein the needle is concentrical relative to the distal end of the catheter.

22. The method of claim 13, wherein the therapeutic intervention comprises:
insufflating the pericardial space;
monitoring a pressure outside of the heart;
positioning a heart implant or instrument exterior to the heart;
irrigating an exterior of the heart;
suctioning bleeding;
draining pericardial fluid;
performing an epicardial biopsy; mapping a portion of the heart; or pacing the heart.

* * * * *